(12) United States Patent
Neff et al.

(10) Patent No.: US 9,764,103 B2
(45) Date of Patent: Sep. 19, 2017

(54) SALT PUFFER

(71) Applicants: Lily A. Neff, Mesa, AZ (US); Edward J. Neff, Mesa, AZ (US)

(72) Inventors: Lily A. Neff, Mesa, AZ (US); Edward J. Neff, Mesa, AZ (US)

( * ) Notice: Subject to any disclaimer, the term of this patent is extended or adjusted under 35 U.S.C. 154(b) by 734 days.

(21) Appl. No.: 14/047,761

(22) Filed: Oct. 7, 2013

(65) Prior Publication Data

US 2014/0096770 A1    Apr. 10, 2014

Related U.S. Application Data

(60) Provisional application No. 61/710,208, filed on Oct. 5, 2012.

(51) Int. Cl.
*A61M 15/00* (2006.01)
*A61M 16/00* (2006.01)
(Continued)

(52) U.S. Cl.
CPC .... *A61M 15/0091* (2013.01); *A61M 16/0666* (2013.01); *A61M 16/105* (2013.01); *A61M 15/0098* (2014.02); *A61M 15/085* (2014.02); *A61M 16/0057* (2013.01); *A61M 16/0066* (2013.01); *A61M 16/208* (2013.01);
(Continued)

(58) Field of Classification Search
CPC .......... A61M 15/0091; A61M 15/0098; A61M 15/085; A61M 2016/0027; A61M 2016/0039; A61M 16/0057; A61M 16/0066; A61M 16/0666; A61M 16/105; A61M 16/1055; A61M 16/208; A61M 2205/3569; A61M 2205/3592; A61M 2205/584; A61M 2205/8218;
(Continued)

(56) References Cited

U.S. PATENT DOCUMENTS 2,470,297 A * 5/1949 Fields .................. A61M 15/00
                                                       128/203.15
2,503,732 A * 4/1950 Heisterkamp ......... A61M 15/00
                                                       128/203.15
(Continued)

FOREIGN PATENT DOCUMENTS

HU  WO 2004012802 A1 *  2/2004  ............ A61M 15/00
RO            122480 B1 *  7/2009
RO  WO 2009134157 A2 * 11/2009  ............ A61M 15/00

OTHER PUBLICATIONS

English abstract of RO 122480 B1.*

*Primary Examiner* — Tan-Uyen (Jackie) T Ho
*Assistant Examiner* — Joseph D Boecker
(74) *Attorney, Agent, or Firm* — Schmeiser, Olsen & Watts LLP

(57) ABSTRACT

An inhaler/puffer is provided. The inhaler/puffer may comprise a body, a cap, and a base, the cap and the base being configured to functionally engage the body. The body may define a chamber wherein minerals, such as salt, may be housed. The body, cap, and base may be configured to permit a user to inhale on the cap and draw air through the base into the chamber, over the minerals, through the cap and into the respiratory system of the user. Additionally, the inhaler/puffer may be placed in-line with an oxygen breathing system, such that as the breathing system provides oxygen to the user, the user also receives salt air treatment.

18 Claims, 6 Drawing Sheets

(51) Int. Cl.
*A61M 16/10* (2006.01)
*A61M 16/06* (2006.01)
A61M 16/20 (2006.01)
A61M 15/08 (2006.01)

(52) U.S. Cl.
CPC .............. *A61M 2016/0027* (2013.01); *A61M 2016/0039* (2013.01); *A61M 2205/3569* (2013.01); *A61M 2205/3592* (2013.01); *A61M 2205/584* (2013.01); *A61M 2205/8218* (2013.01); *A61M 2205/8237* (2013.01); *A61M 2205/8275* (2013.01)

(58) Field of Classification Search
CPC .. A61M 2205/8237; A61M 2205/8275; A62B 7/02; A62B 7/11; A62B 7/12
See application file for complete search history.

(56) References Cited

U.S. PATENT DOCUMENTS

| | | | | |
|---|---|---|---|---|
| 2,533,065 A * | 12/1950 | Taplin | ............... | A61M 15/0028 128/203.12 |
| 3,027,897 A * | 4/1962 | Carofiglio | ............. | A61M 15/08 128/202.17 |
| 3,556,097 A * | 1/1971 | Wallace | ............... | A61M 16/06 128/202.23 |
| 4,353,365 A * | 10/1982 | Hallworth | ......... | A61M 15/0028 128/203.15 |
| 4,846,168 A * | 7/1989 | Abiko | ............... | A61M 15/0028 128/200.23 |
| 5,787,881 A * | 8/1998 | Chawla | ............. | A61M 15/0028 128/203.15 |
| 6,102,036 A * | 8/2000 | Slutsky | ............. | A61M 15/0045 128/202.21 |
| 6,651,654 B2 * | 11/2003 | Rogacki | ............. | A61M 15/00 128/200.24 |
| 7,048,953 B2 * | 5/2006 | Vail, III | ............... | A61K 36/534 424/1.13 |
| 7,100,605 B2 * | 9/2006 | Opitz | .................... | A61M 15/02 128/202.13 |
| 7,820,210 B2 * | 10/2010 | Vail, III | ................. | A61K 36/53 424/747 |
| 7,832,397 B2 * | 11/2010 | Lipowicz | .............. | A61M 15/06 128/203.12 |
| 8,662,078 B2 * | 3/2014 | Zoltan | ................... | A61M 15/08 128/203.15 |
| 2007/0175476 A1 * | 8/2007 | Lipowicz | .............. | A61M 15/06 128/205.29 |
| 2008/0163871 A1 * | 7/2008 | Bozoky | ................. | A61M 15/02 128/203.27 |
| 2009/0232895 A1 * | 9/2009 | Pascu | ................... | A61K 9/0075 424/489 |
| 2012/0126043 A1 * | 5/2012 | Viherlahti | ........... | A61K 9/0075 241/5 |
| 2012/0247463 A1 * | 10/2012 | Zoltan | ................... | A61M 15/08 128/203.15 |
| 2015/0283352 A1 * | 10/2015 | Karkkainen | .......... | A61M 16/16 128/203.26 |

* cited by examiner

SALT PUFFER

CROSS REFERENCE TO RELATED APPLICATION[S]

This application claims priority to U.S. Provisional Patent Application to Neff entitled "SALT PUFFER," Ser. No. 61/710,208, filed Oct. 5, 2012, the disclosure of which is hereby incorporated entirely herein by reference.

BACKGROUND

Technical Field

This disclosure relates generally to health and wellness breathing devices.

State of the Art

Salt Cave Therapy (Speleotherapy) is a known method for assisting health and wellness. As the person breaths in the salt-filled air in the caves, the minerals in the salt-filled air enter into the person and the salt-filled mineral air cleans up, regenerates and heals the irritated and inflamed breathing system of the person. The substances locked in the salt crystals for millions of years do their job and go down to the most hidden corners of the person's breathing system on a micro level and once there, aide the person's body in cleaning the respiratory system. The salt is a natural anti-bacterial that kills germs that cause infections.

However, traveling to these caves was/is very costly and time-consuming. As a result, persons could not reach and utilize this salt cave breathing treatment on a regular basis for the related health benefits. Eventually, hand-held inhalers have been developed based on the salt cave therapy and have made it more convenient to for users to obtain the benefits of salt cave therapy. Indeed, these inhalers have largely replaced traveling to the cave.

Many of these inhalers are made of ceramic or porcelain. The ceramic may chip, flake, break off, or otherwise fragment and leave undesired ceramic particles mixed in with the salt or minerals within the ceramic inhaler. Also, many of these inhalers have small inlet holes for inserting salt therein. This makes it difficult of the user to insert the salt within the inhaler. Moreover, it becomes increasing more difficult to take the salt out and clean the inhaler should the salt begin to clump, due to moisture, into a large mass that is larger than the small inlet hole. As a result, these inhalers are riddled with problems, such as being difficult to sanitize, being fragile, and being cumbersome to transport from location to location and/or carry around on the user.

Thus, there is a need in the market for a device that addresses these concerns and makes it more convenient and efficient for persons to receive Speleotherapy.

SUMMARY

The present disclosure relates to health and wellness breathing devices.

An aspect of the present disclosure includes an inhaler, the inhaler comprising a tubular body having a first region and a second region, the tubular body defining a chamber between the first region and the second region, the chamber being configured to house a dry material therein, a cap having a first end and a second end, the first end comprising an opening, the second end being configured to be releasably coupled to the tubular body at the first region, a base configured to be releasably coupled to the tubular body at the second region, the base being configured to permit fluidic communication through the base and into the chamber, and a filter member within the tubular body and configured to permit fluidic communication between the chamber and the cap.

Another aspect of the present disclosure includes wherein the filter member is fixedly coupled to sidewalls of the body between the first region and the second region and is configured to prevent the dry material from entering the cap.

Another aspect of the present disclosure includes wherein the cap tapers from the second end to the first end.

Another aspect of the present disclosure includes wherein the base is comprised of synthetic material and the cap and the base are each comprised of high density rubber.

Another aspect of the present disclosure includes wherein the dry material is crystalline salt.

Another aspect of the present disclosure includes wherein the cap is configured to be removed from the inhaler without releasing the dry material from the chamber.

Another aspect of the present disclosure includes wherein the base is as wide as the tubular body.

Another aspect of the present disclosure includes wherein under a condition that a user places his/her mouth over the opening and inhales on the cap, fluid flows through the base, into the chamber, through the salt, through the filter member, through the cap, and out of the opening into the user's respiratory system.

Another aspect of the present disclosure includes a breathing system, the system comprising an oxygen delivery system having a tube coupled from an oxygen tank to a user, the tube delivering oxygen from the oxygen tank to the user, an inhaler configured in line with the tube, the inhaler comprising a tubular body having a first region and a second region, the tubular body defining a chamber between the first region and the second region, the chamber being configured to house a dry material therein, a cap having a first end and a second end, the first end having a receptor for coupling to the tube, the second end being configured to be releasably coupled to the tubular body at the first region, a base having a first end and a second end, the first end being configured to be releasably coupled to the tubular body at the second region, the second end having a receptor for coupling to the tube, the base being configured to permit fluidic communication through the base and into the chamber, and a filter member within the tubular body and configured to permit fluidic communication between the chamber and the cap.

Another aspect of the present disclosure includes wherein under a condition the oxygen delivery system operates to deliver oxygen from the oxygen tank to the user, the oxygen enters the inhaler and flows through the base, into the chamber, through the salt, through the filter member, through the cap, and into the tube leading to the user's respiratory system.

Another aspect of the present disclosure includes a speleotherapy breathing treatment method, the method comprising providing an inhaler having a base, a body, and a cap, removing a base from the body, inserting salt crystals into the body, coupling the base to the body to retain the salt crystals in the body, coupling the cap to the body, and inhaling on the cap to draw air through the base, over the salt in the body, through the cap and into the respiratory system.

Another aspect of the present disclosure includes removing the cap from the body while maintaining the salt crystals within the body.

Another aspect of the present disclosure includes disassembling the inhaler by removing the base and the cap from the body.

Another aspect of the present disclosure includes inserting the inhaler in line with an oxygen delivery system, such that the oxygen delivery system forces oxygen through the base, over the salt in the body, through the cap and into the respiratory system.

The foregoing and other features, advantages, and construction of the present disclosure will be more readily apparent and fully appreciated from the following more detailed description of the particular embodiments, taken in conjunction with the accompanying drawings.

BRIEF DESCRIPTION OF THE DRAWINGS

Some of the embodiments will be described in detail, with reference to the following figures, wherein like designations denote like members.

DETAILED DESCRIPTION OF EMBODIMENTS

A detailed description of the hereinafter described embodiments of the disclosed apparatus and method are presented herein by way of exemplification and not limitation with reference to the Figures listed above. Although certain embodiments are shown and described in detail, it should be understood that various changes and modifications may be made without departing from the scope of the appended claims. The scope of the present disclosure will in no way be limited to the number of constituting components, the materials thereof, the shapes thereof, the relative arrangement thereof, etc., and are disclosed simply as an example of embodiments of the present disclosure.

As a preface to the detailed description, it should be noted that, as used in this specification and the appended claims, the singular forms "a", "an" and "the" include plural referents, unless the context clearly dictates otherwise.

Figure 1:
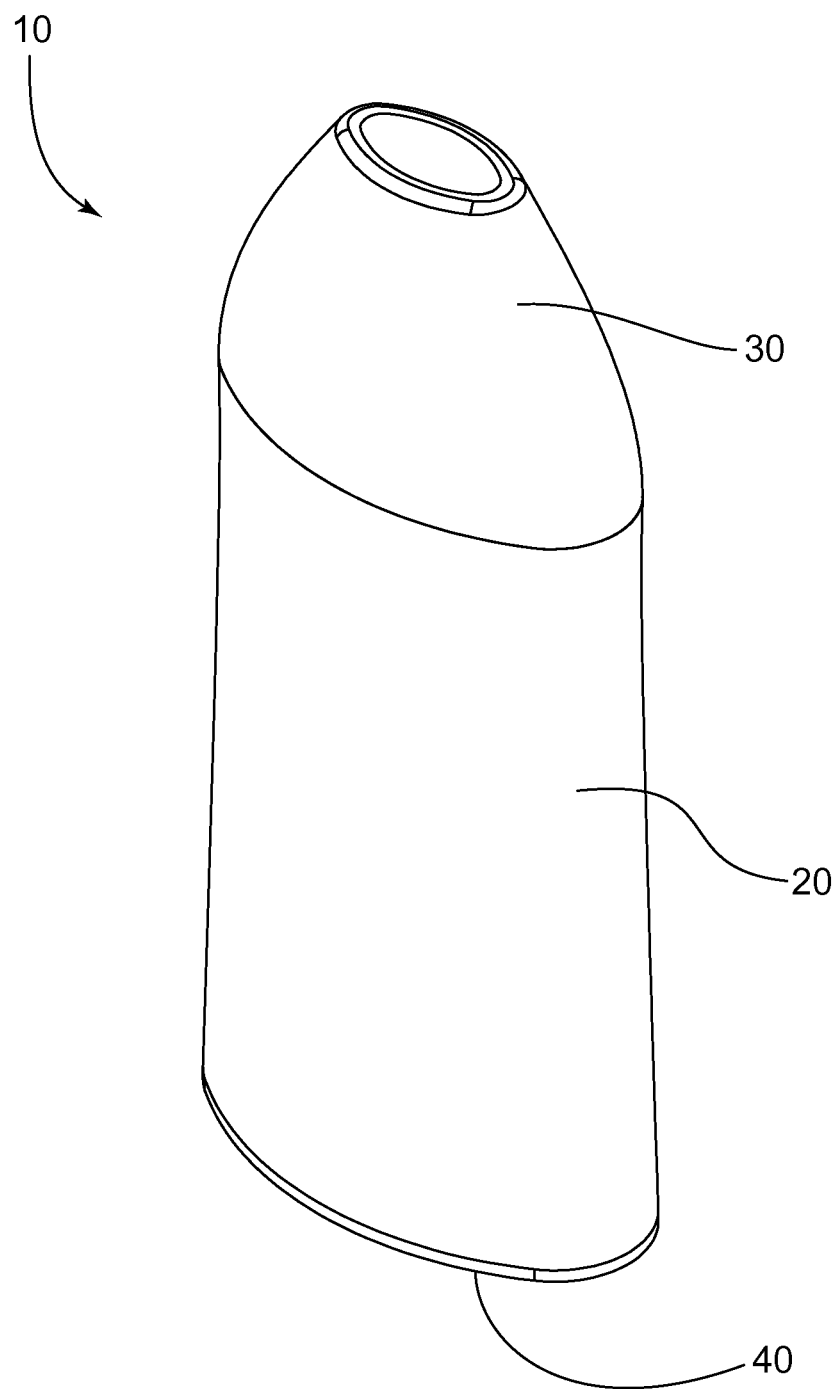
FIG. 1 is a perspective view of an embodiment of a salt puffer/inhaler in accordance with the present disclosure.
Figure 2:
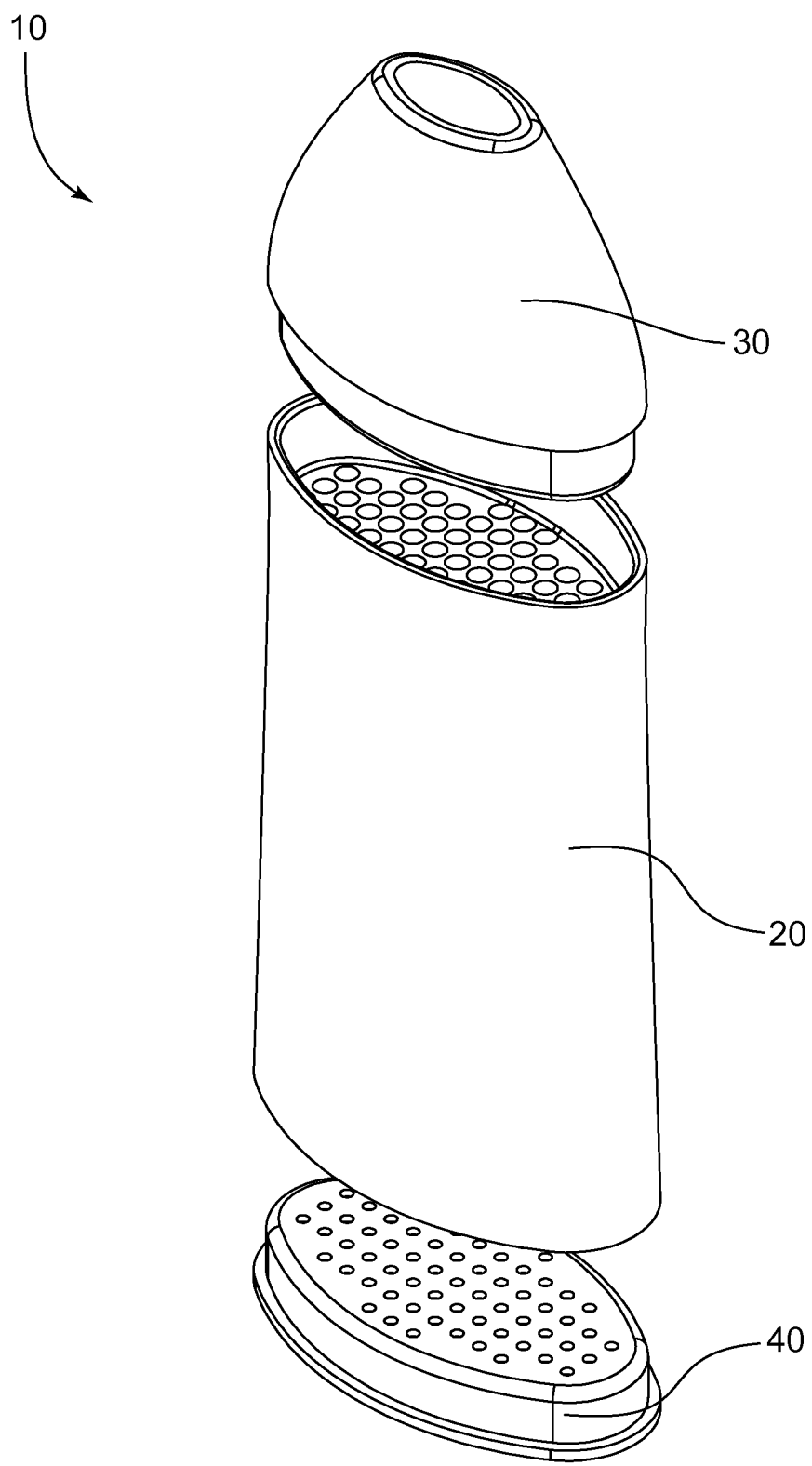
FIG. 2 is an exploded perspective view of the embodiment of a salt puffer/inhaler depicted in FIG. 1 in accordance with the present disclosure.

Referring to the drawings, FIGS. 1 and 2 depict an embodiment of an inhaler/puffer 10 that may comprise various structural components that complement one another to provide the unique functionality and performance of the inhaler/puffer 10, the structure and function of which will be described in greater detail herein. Embodiments of the inhaler/puffer 10 may comprise, among other components, a body 20, a cap 30, and a base 40, the cap 30 and the base 40 being configured to functionally engage the body 20. The body 20 may be comprised of high-quality, BPA-free, injection molded plastic or other similar synthetic materials. The cap 30 and base 40 may be made of the same high-quality, BPA-free, injection molded plastic or other similar synthetic materials. Alternatively, the cap 30 and base 40 may be made of a high-density rubber compound, which may be more comfortable to the user who may place his/her mouth to the cap 30 to use the inhaler/puffer 10. Moreover, the rubber material of the base 40 and cap 30 may better interact with the body 20 to functionally engage the base 40 and the cap 30 to the body 20.

Figure 3:
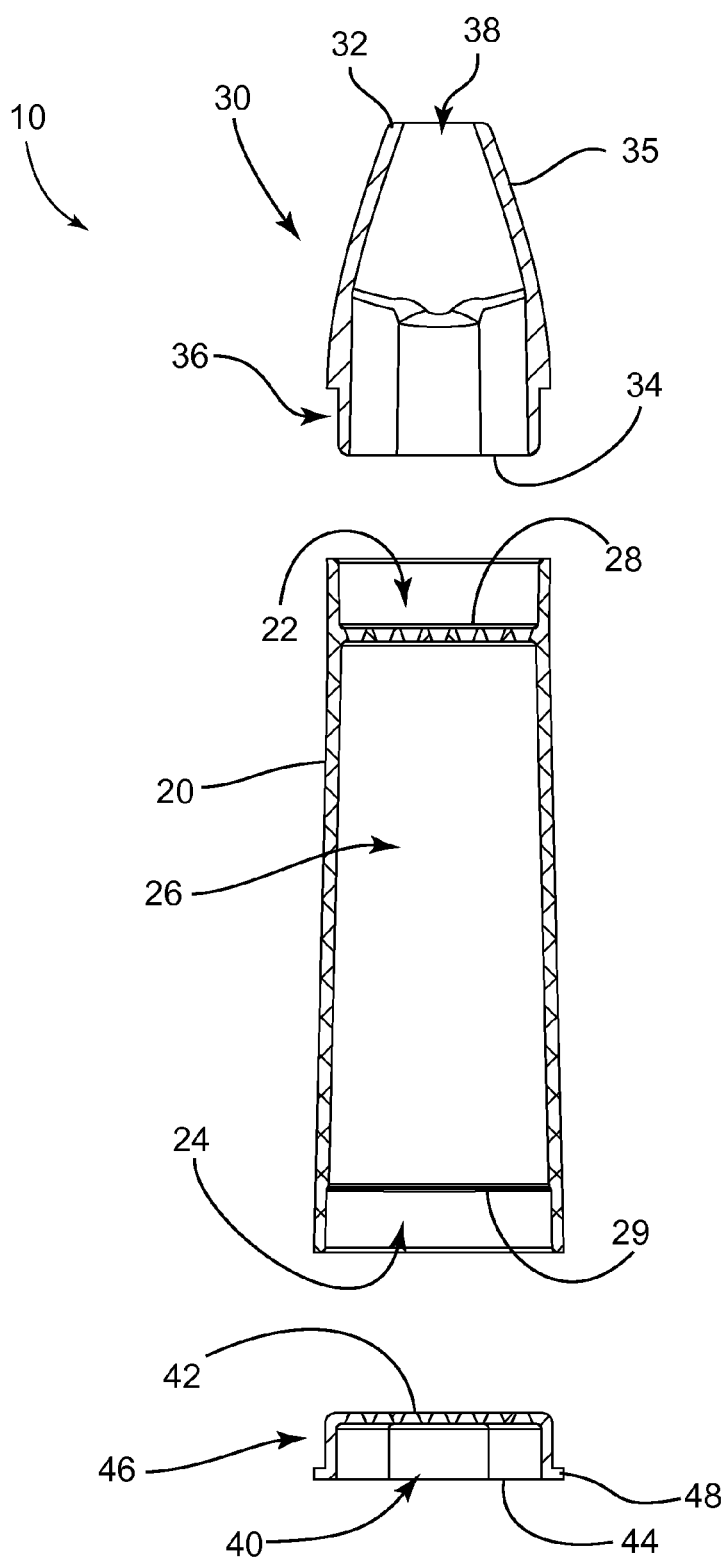
FIG. 3 is an exploded side view of the embodiment of a salt puffer/inhaler depicted in FIG. 1 in accordance with the present disclosure.
Figure 4:
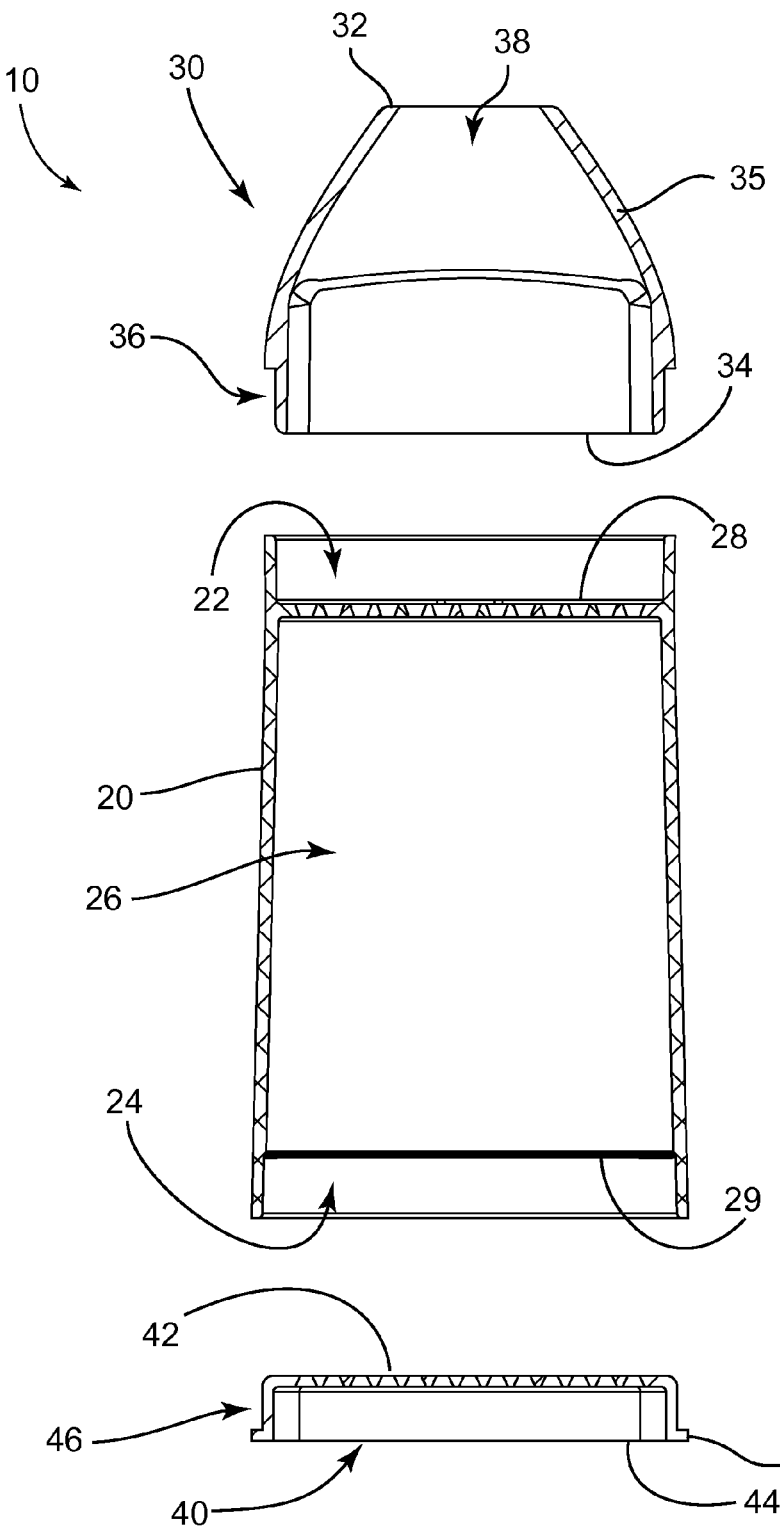
FIG. 4 is an exploded front view of the embodiment of a salt puffer/inhaler depicted in FIG. 1 in accordance with the present disclosure.

Referring to the drawings, FIGS. 3 and 4 depict an embodiment of the inhaler/puffer 10 that may further comprise a body 20 having a first region 22 and a second region 24. The first region 22 may be defined in one end of the body 20 and may further be defined by a filter member 28. The filter member 28 may be perforated, pierced, comprised of holes, or otherwise configured to permit fluidic flow of air or other fluid mediums through the filter member 28. The filter member 28 may function as a screen. The filter member 28 may be fixedly configured in an internal portion of the body 20. The filter member 28 may define the upper metes and bounds of the chamber 26. The walls of the body 20 may further define the sides of the chamber 26. The base 40 may define the lower metes and bounds of the chamber 26. The first region 22 may be configured to receive the cap 30 therein and functionally engage the cap 30 to releasably secure the cap 30 to the body 20. The second region 24 may be defined in one end of the body 20 opposite the first region 22 and may further be defined by an internal lip 29. The second region 24 may be configured to receive the base 40 therein and functionally engage the base 40 to releasably secure the base 40 to the body 20. The body 20 may further define a chamber 26, the chamber 26 being hollow or vacant, but configured to hold, store, or otherwise retain a material, such as salt or other minerals in the case of a salt inhaler/puffer. The body 20 may have a length and be tubular in shape. Further, the body 20 may have an oval cross-sectional shape. The body 20 may further have other shapes, so long as the shape of the body 20 is convenient to hold in the user's hand.

Embodiments of the inhaler/puffer 10 that may further comprise a cap 30 having a first end 32 and a second end 34. The cap 30 may define an hollow interior, the second end 34 may be open, and the first end 32 may define an opening 38 therein that is smaller in diameter or size than the open second end 34. For example, the first end 32 may have a taper 35 from the width or diameter of the second end 34 to a smaller width or diameter of the first end 32. Thus, the opening 38 may be relatively smaller than the open second end 34. The second end 34 may further comprise an engagement region 36 defined in an exterior portion of the second end 34. The engagement region 36 may be configured to functionally engage the first region 22 of the body 20. For example, the engagement region 36 may be configured to slide or slip within the first region 22, make physical contact with the first region 22 such that a friction fit is established between the engagement region 36 and the first region 22 to retain the cap 30 in functional communication with the body 20. The configuration of the cap 30 may permit a user to place the cap 30 in his/her mouth and breathe to draw air, oxygen, or other fluid through the base 40, into the chamber 26 of the body 20 to pass over or through the medium, such as salt, placed therein, and through the cap 30 to flow out of the opening 38 and into the user's mouth and lungs.

Embodiments of the inhaler/puffer 10 may further comprise a base 40 having a first end 42 and a second end 44. The first end 42 of the base 40 may be configured to be perforated, pierced, comprised of holes, or otherwise configured to permit fluidic flow of air or other fluid mediums through the base 40 and into the chamber 26 of the body 20. The base 40 may further comprise an engagement region 46 defined in an exterior portion of the base 40. The engagement region 46 may be configured to functionally engage the second region 24 of the body 20. The base 40 may function as a plug for the lower regions of the body 20. For example, the engagement region 46 may be configured to slide or slip within the second region 24, make physical contact with the second region 24 such that a friction fit is established between the engagement region 46 and the second region 24 to retain the base 40 in functional communication with the body 20. The base 40 may further comprise an exterior lip 48 proximate the engagement region 46. The lip 48 may be configured to prevent the base 40 from being inserted too far into the second region 24. For example, the lip 48 may engage the distal end or exterior wall of the body 20. Moreover, the first end 42 may be configured to functionally engage the internal lip 29 to effectively couple the base 40 to the body 20 and enclose the medium within the chamber 26.

Embodiments of the inhaler/puffer 10 may comprise the user being able to breathe salt-filled air through the inhaler/puffer 10. For example, a user may place salt or other mineral mediums within the chamber 26. Thereafter, the user may couple the base 40 to the body 20 to effectively seal the salt or other mineral medium within the chamber 26. The cap 30 may be placed on the body 20 to provide a convenient means for the user to place his/her mouth over the opening 38 in the cap 30 to breathe and draw air, oxygen, or other fluid through the base 40, into the chamber 26 of the body 20 to pass over or through the medium, such as salt, placed therein, and through the filter member 28 and the cap 30 to flow out of the opening 38 and into the user's mouth and lungs. The base 40 may prevent salt crystals or other mineral mediums from passing therethrough or falling out of the body 20. Likewise, the filter member 28 may be configured to prevent salt crystals or other mineral mediums from passing therethrough or being inhaled out of the body 20 and through the cap 30 into the user's mouth and/or lungs. Yet, the base 40 and the filter member 28 are configured to permit fluid flow therethrough, such that the fluid flow over the dry material in the chamber 26, may pick up the airborne vapors and other healthy components, including microscopic breathable particles, of the dry material and transport the airborne vapors and other healthy components into the user's mouth, lungs, and respiratory system.

The configuration of the cap 30 and the base 40 both being removable from the body 20 include several advantages and benefits over other conventional salt inhalers. For example, the cap 30 may be removed from the body 20 and the cap 30 may be sanitized without having to remove the salt from the body 20. Indeed, the cap 30 may be removed from the remainder of the inhaler/puffer 10, such that the cap 30 may be cleaned and sanitized separate and apart from the remainder of the inhaler/puffer 10. In this way, the user of the inhaler/puffer 10 may clean and sanitize the cap 30, which is the one component of the inhaler/puffer 10 to which the user's mouth is placed, without having to disturb the remaining components of the inhaler/puffer 10. This makes the act of sharing the inhaler/puffer 10 between two or more users much more convenient and plausible. Indeed, each user may utilize his/her own cap 30 and place this cap 30 on the inhaler/puffer 10 to use the inhaler/puffer 10 and then remove the cap 30 to share the inhaler/puffer 10 with another user who has his/her own cap 30.

Further, when the user desires to clean the body 20, the base 40 may be easily removed from the body 20, the salt may be emptied from the chamber 26 and all portions of the base 40 and body 20, including internal regions, such as the chamber 26, may be easily accessible to cleaning. Embodiments of the inhaler/puffer 10 include the base 40 being as wide or long as the opening of the chamber 26, such that if the salt or mineral medium clumps in the chamber 26 due to moisture, the entire clump of salt may be removed easily by removing the base 40 from the body 20. In addition to the ease of sanitation and cleaning, the removable parts of the inhaler/puffer 10 provide that if one part of the inhaler/puffer 10 break or become unusable, a replacement part may be inserted thereon and used, instead of the entire inhaler/puffer 10 needing to be replaced. Also, because the entire base 40 may be removed from the body 20 to expose the chamber 26, it is relatively easy for a user to place the salt or other mineral medium within the chamber 26.

Embodiments of the inhaler/puffer 10 may further comprise the inhaler/puffer 10 being sized to be easily portable by a user. For example, the inhaler/puffer 10 may be sized to fit within the front shirt pocket of a men's dress shirt. Further in example, the inhaler/puffer 10 may be sized to fit within the pants pocket of a pair of pants. Further in example, the inhaler/puffer 10 may be sized to fit within a women's handbag. In addition to its portability and convenience in handling and transportation, the inhaler/puffer 10 may further be designed of materials that resist and even prevent breakage due to forces exerted on the inhaler/puffer 10. As mentioned herein, the body 20 may be comprised of high-quality, BPA-free, injection molded plastic or other similar synthetic materials that are resistant and can prevent breakage of the body 20 from forces exerted on the body 20 under normal operating conditions or normal transportation conditions. Further, the body 20 may be configured of materials that resist breakage under heavy forces exerted on the body 20 from other than normal operating conditions or normal transportation conditions that may otherwise break or shatter conventional ceramic inhalers. The cap 30 and base 40 may be made of the same high-quality, BPA-free, injection molded plastic or other similar synthetic materials to achieve the same preventative characteristics against breakage. Further, the cap 30 and base 40 may be configured of materials that resist breakage under heavy forces exerted on the cap 30 and base 40 from other than normal operating conditions or normal transportation conditions that may otherwise break or shatter conventional ceramic inhalers. Alternatively, the cap 30 and base 40 may be made of a high-density rubber compound, which may be more comfortable to the user who may place his/her mouth to the cap 30 to use the inhaler/puffer 10. Such a rubber compound may be configured to bend or flex in response to forces exerted therein, and thereby resist breakage that might otherwise result. Further, the cap 30 and base 40 may be configured of these rubber materials that resist breakage and flex under heavy forces exerted on the cap 30 and base 40 from other than normal operating conditions or normal transportation conditions that may otherwise break or shatter conventional ceramic inhalers. For example, if conventional inhalers are dropped, the force of impact may crack, split, fracture, shatter, or otherwise damage the conventional inhaler, whereas the inhaler/puffer 10 may resist such forces.

Figure 5:
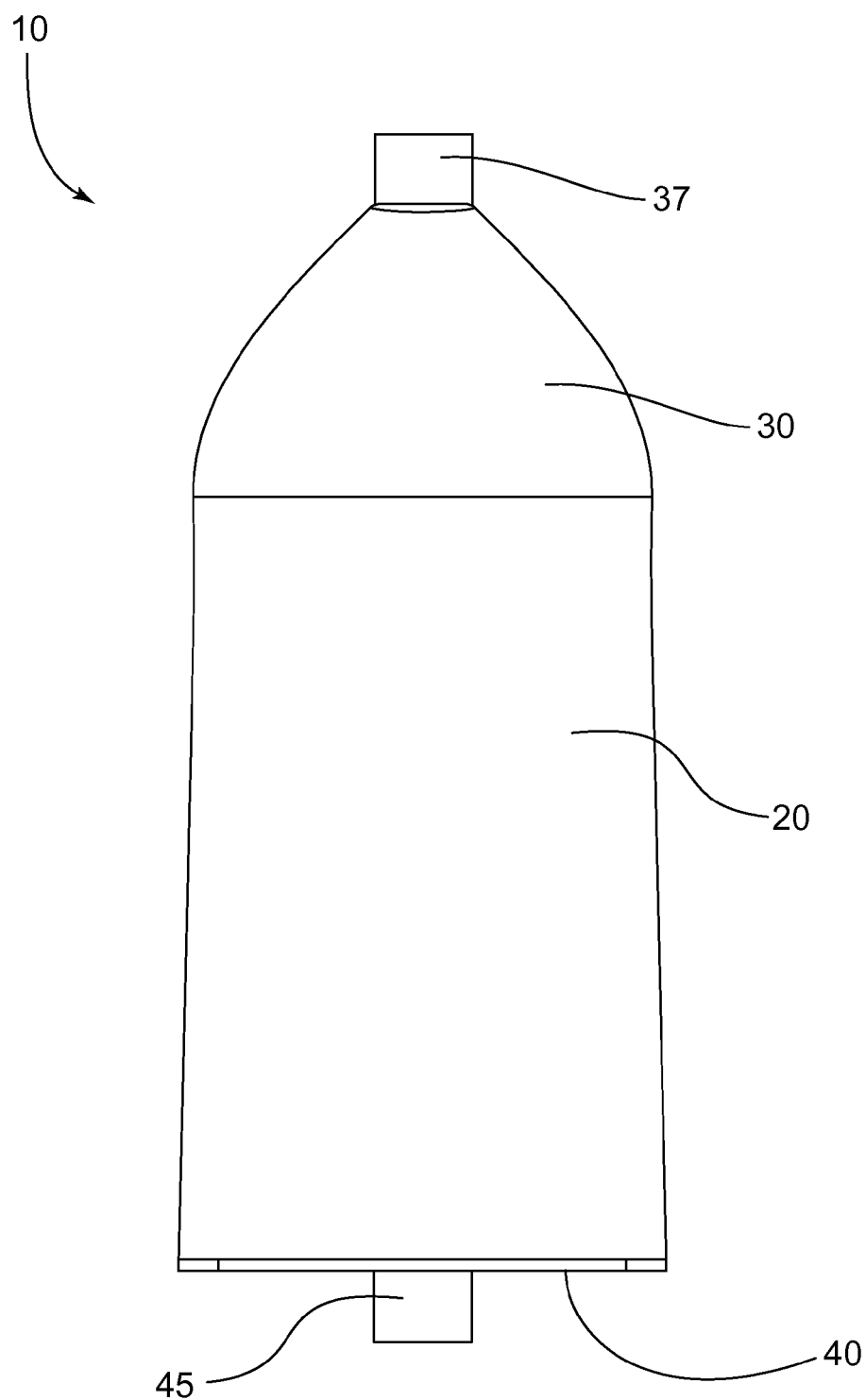
FIG. 5 is a front view of an embodiment of a salt puffer/inhaler in accordance with the present disclosure.
Figure 6:
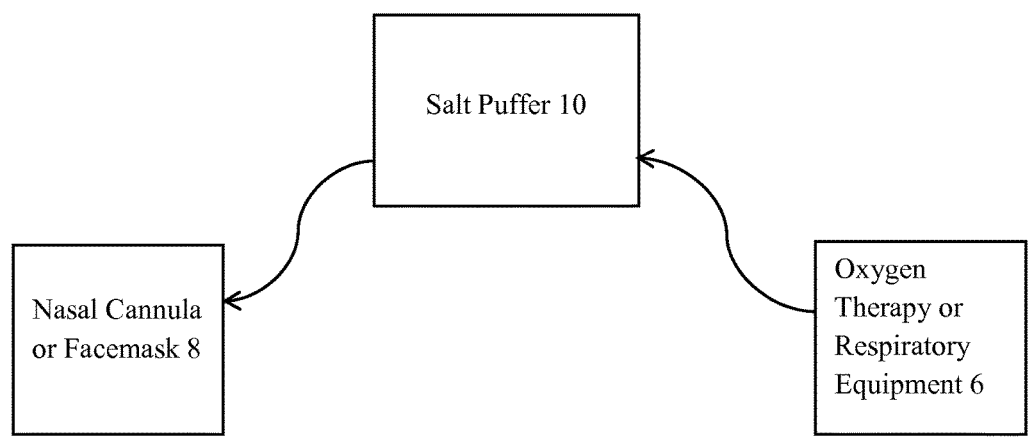
FIG. 6 is a schematic view of an embodiment of a salt puffer/inhaler system in accordance with the present disclosure.

Referring to the drawings, FIG. 5 depicts an embodiment of the inhaler/puffer 10 that may further comprise a base 40 having a receptor 45 configured thereon. The receptor 45 may be configured as part of the base 40 and structured to receive and functionally couple to tubing or other flexible member of an oxygen delivery system 6 or oxygen breathing device that assists a user in the act of breathing or at least passively provides oxygen to the user. With the tubing functionally coupled to the receptor 45, the oxygen provided from the device 6 may pass through the tubing, into the receptor 45, through the base 40, into the chamber 26, over the dry substances housed therein, through the filter element 28, through the cap 30 and into tubing or other flexible member functionally coupled to the cap 30, such that the salt-filled oxygen air that has passed through the inhaler/puffer 10, may travel through the tubing or flexible member and into a nasal cannula 8 or facemask 7 on a user. In other words, as depicted in FIG. 6, the inhaler/puffer 10 having the receptor 45 thereon, may be placed in-line with the oxygen breathing device, such that the user may receive Speleotherapy treatment at the same time as receiving oxygen treatment. As a result, the user does not need to bring the inhaler/puffer 10 to his/her mouth to receive Speleotherapy treatment. Moreover, due to the pressure provided by the oxygen delivery system 6, the inhaler/puffer 10 is protected from the user exhaling back into the inhaler/puffer 10 which may transmit humid/moist breath down into the salt crystals, or other minerals, to clump the salt crystals together. The tubing leading from the inhaler/puffer 10 to the user's nasal cannula 8 or facemask 7 may be inserted within the opening 38 to functionally engage and couple to the cap 30. Further, the cap 30 may be configured to have a receptor 37 that is structured similarly to the receptor 45 on the base 40. The receptor 37 may be configured much like receptor 45 to receive and functionally couple to tubing or other flexible member of an oxygen breathing device 6.

Embodiments of the inhaler/puffer 10 may further comprise a cap 30' being configured similarly to the base 40, in that the cap 30' may be shaped substantially similar to the base 40. For example, instead of the cap 30' having the shape and configuration of the cap 30 depicted in FIGS. 1-5, the cap 30' may appear in shape, structure and function more like the base 40 of FIGS. 1-5. In other words, embodiments of the inhaler/puffer 10 may comprise a base 40 being releasably coupled to the body 20, as depicted in FIGS. 1-5, and a cap 30', that appears in shape and structure similar to that of the base 40 in FIGS. 1-5, being coupled to the body 20 on the opposing side of the body 20. Receptor 37 may be positioned on cap 30' much like the receptor 45 is positioned on the base 40. Therefore, embodiments of the inhaler/puffer 10 may comprise the base 40 having the receptor 45 thereon being coupled to the second region 24 of the body 20, and the cap 30' (that is shaped like the base 40 and the receptor 45) having the receptor 37 thereon being coupled to the first region 22 of the body 20.

Embodiments of the inhaler/puffer 10 may further comprise a cap 30 without the receptor 37, a cap with the receptor 37 thereon, a base without the receptor 45, and/or a base with the receptor 45 thereon. Such components may be interchangeable according to the individual needs of the user.

While this disclosure has been described in conjunction with the specific embodiments outlined above, it is evident that many alternatives, modifications and variations will be apparent to those skilled in the art. Accordingly, the preferred embodiments of the present disclosure as set forth above are intended to be illustrative, not limiting. Various changes may be made without departing from the spirit and scope of the present disclosure, as required by the following claims. The claims provide the scope of the coverage of the present disclosure and should not be limited to the specific examples provided herein.

What is claimed is:
1. An inhaler, the inhaler comprising:
a tubular body having a first region and a second region, the tubular body defining a chamber between the first region and the second region, the chamber housing salt crystals therein;
a flexible cap having a first end and a second end, the first end comprising an opening, the second end being open and comprising an engagement region releasably coupled within the tubular body at the first region by a friction fit;
a flexible base releasably coupled within the tubular body at the second region by a friction fit, the base comprising a plurality of holes to permit fluidic communication through the base and into the chamber and through the chamber and out the base and wherein the holes are smaller than the salt crystals to prevent the salt crystals from passing through the plurality of holes of the base; and
a filter member formed as a unitary part of the tubular body, the filter member comprising a plurality of holes to permit fluidic communication between the chamber and the cap and wherein the holes are smaller than the salt crystals to prevent the salt crystals from passing through the plurality of holes of the filter member, wherein the chamber housing the salt crystals is bound on one end by the base and an opposite end by the filter member.

2. The inhaler of claim 1, wherein the filter member is fixedly coupled to sidewalls of the tubular body between the first region and the second region and is configured to prevent the salt crystals from entering the cap.

3. The inhaler of claim 1, wherein the cap tapers from the second end to the first end.

4. The inhaler of claim 1, wherein the tubular body is comprised of synthetic material and the cap and the base are each comprised of high density rubber.

5. The inhaler of claim 1, wherein the cap is configured to be removed from the inhaler without releasing the salt crystals from the chamber.

6. The inhaler of claim 1, wherein the base is as wide as the tubular body.

7. The inhaler of claim 1, wherein under a condition that a user places his/her mouth over the opening and inhales on the cap, fluid flows through the base, into the chamber, through the salt, through the filter member, through the cap, and out of the opening into the user's respiratory system.

8. A breathing system, the system comprising:
an oxygen delivery system having a tube coupled from an oxygen tank to a user, the tube delivering oxygen from the oxygen tank to the user;
an inhaler configured in line with the tube, the inhaler comprising:
a tubular body having a first region and a second region, the tubular body defining a chamber between the first region and the second region, the chamber housing salt crystals therein;
a flexible cap having a first end and a second end, the first end comprising an opening, the second end being open and comprising an engagement region releasably coupled within the tubular body at the first region by a friction fit;
a flexible base having a first end and a second end, the first end being releasably coupled to the tubular body at the second region, the second end having a receptor for coupling to the tube, the base permitting fluidic communication through the base and into the chamber; and
a filter member formed as a unitary part of the tubular body, the filter member comprising a plurality of holes to permit fluidic communication between the chamber and the cap and wherein the holes are smaller than the salt crystals from passing through the plurality of holes of the filter member, wherein the chamber housing the salt crystals is bound on one end by the base and on an opposite end by the filter member.

9. The system of claim 8, wherein the filter member is fixedly coupled to sidewalls of the tubular body between the first region and the second region and is configured to prevent the salt crystals from entering the cap.

10. The system of claim 8, wherein the cap tapers from the second end to the first end.

11. The system of claim 8, wherein the tubular body is comprised of synthetic material and the cap and the base are each comprised of high density rubber.

12. The system of claim 8, wherein the cap is configured to be removed from the inhaler without releasing the salt crystals from the chamber.

13. The system of claim 8, wherein the base is as wide as the tubular body.

14. The system of claim 8, wherein under a condition that the oxygen delivery system operates to deliver oxygen from the oxygen tank to the user, the oxygen enters the inhaler and flows through the base, into the chamber, through the salt, through the filter member, through the cap, and into a second tube leading to the user's respiratory system.

15. A speleotherapy breathing treatment method, the method comprising:
providing an inhaler, the inhaler comprising:
a tubular body having a first region and a second region, the tubular body defining a chamber between the first region and the second region, the chamber housing salt crystals therein;
a flexible cap having a first end and a second end, the first end comprising an opening, the second end being open and comprising an engagement region releasably coupled within the tubular body at the first region by a friction fit;
a flexible base releasably coupled within the tubular body at the second region by a friction fit, the base comprising a plurality of holes to permit fluidic communication through the base and into the chamber and through the chamber and out the base and wherein the holes are smaller than the salt crystals to prevent the salt crystals from passing through the plurality of holes of the base; and
a filter member formed as a unitary part of the tubular body, the filter member comprising a plurality of holes to permit fluidic communication between the chamber and the cap and wherein the holes are smaller than the salt crystals to prevent the salt crystals from passing through the plurality of holes of the filter member, wherein the chamber housing the salt crystals is bound on one end by the base and on an opposite end by the filter member;
removing the base from the body;
inserting the salt crystals into the body;
coupling the base to the body to retain the salt crystals in the body;
coupling the cap to the body; and
inhaling on the cap to draw air through the base, over the salt in the body, through the cap and into a respiratory system.

16. The method of claim 15, further comprising removing the cap from the body while maintaining the salt crystals within the body.

17. The method of claim 15, further comprising disassembling the inhaler by removing the base and the cap from the body.

18. The method of claim 15, further comprising inserting the inhaler in line with an oxygen delivery system, such that the oxygen delivery system forces oxygen through the base, over the salt in the body, through the cap and into the respiratory system.

* * * * *